United States Patent
Kershman et al.

(10) Patent No.: US 6,541,025 B1
(45) Date of Patent: *Apr. 1, 2003

(54) METHOD FOR PREPARING SOLID DELIVERY SYSTEM FOR ENCAPSULATED AND NON-ENCAPSULATED PHARMACEUTICALS

(75) Inventors: Alvin Kershman, Chesterfield, MO (US); Jeff L. Shear, Chesterfield, MO (US)

(73) Assignee: Shear/Kershman Laboratories, Inc., Chesterfield, MO (US)

( * ) Notice: Subject to any disclaimer, the term of this patent is extended or adjusted under 35 U.S.C. 154(b) by 84 days.

This patent is subject to a terminal disclaimer.

(21) Appl. No.: 09/656,297

(22) Filed: Sep. 6, 2000

Related U.S. Application Data

(63) Continuation-in-part of application No. 09/476,483, filed on Dec. 30, 1999, now Pat. No. 6,340,471.

(51) Int. Cl.⁷ ................................. A61K 9/20
(52) U.S. Cl. .................. 424/439; 424/441; 424/464; 424/465; 514/778; 514/781; 514/783; 514/951
(58) Field of Search ................. 424/439, 442, 424/489, 484, 498, 441, 464, 465, 490

(56) References Cited

U.S. PATENT DOCUMENTS

| | | |
|---|---|---|
| 2,238,973 A | 4/1941 | Climenko |
| 3,238,103 A | 3/1966 | Vogenthaler |
| 3,253,988 A | 5/1966 | Scott |
| 3,456,050 A | 7/1969 | Rieckmann et al. |
| 3,843,778 A | 10/1974 | Diamond et al. |
| 4,327,076 A | 4/1982 | Puglia et al. |
| 4,581,381 A | 4/1986 | Morris et al. |
| 4,749,575 A | 6/1988 | Rotman |
| 4,981,690 A | 1/1991 | Lopez-Berestein et al. |
| 5,032,404 A | 7/1991 | Lopez-Berestein et al. |
| 5,175,002 A | 12/1992 | Torosian |
| 5,525,352 A | 6/1996 | Kontos et al. |
| 5,576,016 A | 11/1996 | Amselem et al. |
| 5,635,200 A * | 6/1997 | Douglas et al. ............. 424/441 |
| 5,662,932 A | 9/1997 | Amselem et al. |
| 5,716,637 A | 2/1998 | Anselem et al. |
| 6,340,471 B1 * | 1/2002 | Kershman et al. .......... 424/439 |

FOREIGN PATENT DOCUMENTS

| | | |
|---|---|---|
| WO | 97/34496 | 9/1997 |
| WO | 99/47122 | 9/1999 |

* cited by examiner

Primary Examiner—James M. Spear
(74) Attorney, Agent, or Firm—Linda L. Lewis; Greensfelder, Hemker & Gale, P.C.

(57) ABSTRACT

The present invention is an oral drug delivery system for delivering unpalatable pharmaceuticals, wherein the pharmaceutical delivery system comprises a lipid, dry particles including at least one pharmaceutical and at least one filler, and a surfactant, wherein the dry particles are continuously coated by the lipid and form a suspension with the lipid, making the pharmaceutical more palatable.

22 Claims, No Drawings

METHOD FOR PREPARING SOLID DELIVERY SYSTEM FOR ENCAPSULATED AND NON-ENCAPSULATED PHARMACEUTICALS

CROSS REFERENCE TO RELATED APPLICATION

The invention is a continuation-in-part of U.S. patent application Ser. No. 09/476,483 filed Dec. 30, 1999 U.S. Pat. No. 6,340,471 and claims priority of said application.

The present invention relates to oral delivery systems suitable for human and veterinary applications. More specifically, the present invention relates to an oral delivery system for cats, dogs and horses, wherein the normally unpalatable pharmaceutical, such as a drug, vitamin, mineral or food supplement, is made palatable, and therefore easily administered. The pharmaceutical is administered in a solid dosage form, wherein the pharmaceutical is carried in a lipid suspension.

FIELD OF THE INVENTION

Background of the Invention

It is known by those skilled in the art that orally administering pharmaceuticals to animals, specifically cats, dogs and horses, can be exceedingly difficult. The animal may reject the entire dose, or parts of the dose, leaving the vet or the owner frustrated in trying to administer the proper amount.

The true test of a delivery system for animals is whether the pharmaceutical is successfully administered repeatedly. As is often the case, when treating an illness or even a permanent condition of an animal, doses are repeated daily or even several times a day. Once an animal has tasted the unpalatable pharmaceutical that the vet or owner has attempted to hide or disguise, it becomes uncooperative when the administration is repeated. Applicants have discovered a delivery system that presents the pharmaceutical in a palatable form such that the drug can be successfully and easily administered repeatedly.

Heretofore, attempts to alleviate the problem of administering pharmaceuticals have been made a number of ways, including hiding the drug in food. Usually the keen smell of the animal will allow it to detect and reject the pharmaceutical hidden therein. The taste and smell of pharmaceuticals can be masked through the use of flavorings and/or masking agents. Typically, this is only partially successful, as the taste and smell are not completely eliminated.

The pharmaceutical may be microencapsulated, and administered in a gel capsule, but the animal will usually chew the capsule, rupture it, taste the unpalatable pharmaceutical and reject it. Future administrations of the encapsulated pharmaceuticals are thwarted. The use of gel capsules has the additional disadvantages of being costly for delivering large doses of pharmaceuticals. The microencapsulated pharmaceutical may be tabletted using a conventional tablet press. However, such a process invariably damages or ruptures the capsules, defeating the benefits of encapsulation.

The present invention is an oral delivery system, wherein the system delivers microencapsulated pharmaceuticals, wherein the microencapsulation is intact and the pharmaceutical is delivered in a palatable form. Further, the present invention provides the pharmaceutical in a low cost, concentrated form that is easily administered. The delivery system comprises at least one lipid, dry particles including at least one pharmaceutical and at least one filler, and a surfactant, wherein the dry particles are continuously coated by the lipid and form a suspension with the lipid. The suspension exhibits thixotropic or pseudoplastic flow properties. The fillers include cellulose, starch and whey, and comprise from about 60 to 80% of the system (all percentages stated herein are weight percent, unless otherwise indicated). Optionally, flavorings can be added to the dry particles and include cheese, butter, cream, and egg flavorings. Optionally, the pharmaceutical can comprise all of the dry particles, and serve as filler as well as pharmaceutical.

The process for preparing the present delivery system comprises melting the lipid and mixing with the surfactant, blending the dry particles which include the pharmaceutical, filler and, optionally, flavorings with the melted lipid, and pouring or molding the suspension to provide the dose.

U.S. Pat. No. 4,327,076 discloses a compressed chewable antacid tablet which contains from about 10 to 50% active ingredient, from about 2 to 45% fat, from about 25 to 75% fat-sorbing materials, such as starch, and from about 20 to 60% tablet bonders, such as sugars, and surfactants and flavors. The process disclosed by U.S. Pat. No. 4,327,076 involves a pretreatment step wherein the fat is melted and is mixed with fat-sorbing material, tablet bonders and flavorings, forming a fatty powder. The second step involves mixing the active ingredient and surfactant with the pretreated fat and forming a free flowing powder wherein each active ingredient particle is coated with the pretreated fat. The powder thus produced is compressed into chewable pellets.

The above patent fails to disclose the claimed delivery system, wherein the pellets are not compressed into tablets but molded or poured.

U.S. Pat. No. 4,581,381 discloses a chewable antacid pill or pellet containing solid antacid particles having a particle size under 100 millimicrons coated with a fatty material, a surfactant, and a flavoring. The pill or pellet is formed by molding and provides a non-chalky, non-gritty pellet. The antacid particles are coated by melting the fatty material and mixing in the surfactant, the antacid and the flavorings.

The above patent requires very small particles (100 millimicrons), which are not required in the present process.

Neither of the above-referenced patents disclosed the present invention as disclosed and claimed herein.

SUMMARY OF THE INVENTION

The present invention comprises an oral delivery system comprising at least one lipid, at least one surfactant, dry particles including at least one pharmaceutical, and at least one filler, wherein the dry particles are continuously coated by the lipid and form a homogeneous suspension with the lipid. The suspension exhibits thixotropic and/or pseudoplastic properties. The suspension is formed into the desired dose by molding or pouring the suspension when in a liquid or semi-liquid state.

DETAILED DESCRIPTION OF THE INVENTION

The lipids of the present invention may be of animal, vegetable or mineral origin, which are substantially water-insoluble, inert, non-toxic hydrocarbon fats and oils and derivatives thereof, and may comprise any of the commonly commercially available fats or oils approved by the Food & Drug Administration, having melting points in the range of about 90 to 160° F. The lipid may comprise a vegetable oil base commonly known as hard butter. Hard butters are hydrogenated, press fractionated or other processed oils that are processed or recombined to have a solid fat index (percent solid fat vs. temperature) similar to that of cocoa butter. However, other lipids may be used that are relatively hard or solid at room temperature, but melt rapidly in the mouth at a temperature of about 98° F. (mouth temperature). The lipid is employed in the amounts within the range of from about 20 to 40%. Above about 40%, the suspension flows too readily and does not exhibit thixotropic or pseudoplastic flow properties. When present below about 20%, the amount of lipid is not sufficient to completely coat the dry particles.

Examples of suitable lipids include tallow, hydrogenated tallow, hydrogenated vegetable oil, almond oil, coconut oil, corn oil, cottonseed oil, light liquid petrolatum, heavy liquid petrolatum, olein, olive oil, palm oil, peanut oil, persic oil, sesame oil, soybean oil or safflower oil. Additionally, stearines can be used as a lipid in the present invention. The addition of stearines to the product provides the favorable property of mold-release. Further, the addition of stearines raises the melting point of the composition as high as about 100° F., which is particularly beneficial when the product is shipped or stored in unrefridgerated compartments.

The fillers of the present invention are pharmacologically inert and optionally nutritionally beneficial to humans and animals. Such fillers include cellulose such as microcrystalline cellulose, grain starches such as cornstarch, tapioca, dextrin, sugars and sugar alcohols such as sucrose sorbitol, xylitol, mannitol and the like. Preferred fillers include non-fat milk powder, whey, grain brans such as oat bran, and fruit and vegetable pulps. Preferred fillers are finely divided and have a preferred average particle size in the range of about 10 to 500 microns. The fillers are present in the drug delivery device in a concentration of about 60 to 80%. Optionally, the pharmaceutical particles can also serve as filler in the delivery system.

Any emulsifier or surfactant approved for use in foods by the Food and Drug Administration and having a relatively low HLB value, in the range of about 1 to 3, is suitable for use in the present invention. The appropriate surfactant minimizes the surface tension of the lipid, allowing it to oil wet and encapsulate the non-oil solid particles. Typically, the surfactant is present in the delivery system in the concentration of about 0.1 to 1.0%. Suitable surfactants include alkyl aryl sulfonate, or alkyl sulfonates, or sulfonated amides or amines, or sulfated or sulfonated esters or ethers, or alkyl sulfonates, of dioctyl sulfonosuccinate and the like, or a hydrated aluminum silicate such as bentonite or kaolin, triglycerol monostearate, triglycerol monoshortening, octaglycerol monooleate, octaglyceron monostearate, and decaglycerol decaloeate. The preferred surfactant is lecithin.

In the preferred embodiment, the pharmaceutical is microencapsulated. Such microencapsulation includes sustained release encapsulation. Any known method of encapsulation is suitable in the present invention. A preferred method involves slowly blending the drug with a filming agent solution to form granulated particles. The granulated particles are allowed to dry on a tray and are sieved to the desired size, typically in the range of from about 200 to 500 microns. In another embodiment of the present invention, the pharmaceutical is not microencapsulated, but suspended in the lipid as dry particles. Typically the pharmaceutical is present in the delivery device in a concentration of 10% or less. However, the pharmaceutical can comprise all of the dried particles, to provide the necessary dose.

The pharmaceuticals contemplated in the present invention are administered orally. The pharmaceuticals include, but are not limited to, drugs such as analgesics, anti-inflammatory agents, gastrointestinal medications, hormone products, cardiovascular preparations, laxatives and antibiotics. Specific drugs include aspirin, acetaminophen, carpofen, enalapril maleate, furosemide, levothyroxine sodium and prednisolone. Pharmaceuticals further includes vitamins and minerals, as are well known in the art. Pharmaceuticals also includes synthetic and natural food supplements, such as glucosamine, chondroitin, bee pollin, St. John's wort, echninaesia, etc. Additional pharmaceuticals are contemplated for the present invention, and are disclosed in U.S. Pat. No. 4,369,172, which is hereby incorporated by reference.

Optionally, the dry particles include flavorings that make the device taste and smell appealing to humans or animals. The flavorings can be natural or synthetic, and can include butter, milk, cream, egg or cheese. The flavorings are typically present in the device in the range of about 0.05 to 50.0%.

The delivery device may also include other pharmaceutically acceptable agents, such as sweetening agents, including hydrogenated starch hydrolysates, synthetic sweeteners such as sorbitol, xylitol, saccharin salts, L-aspartyl-L-phenylalanine methyl ester, as well as coloring agents, other binding agents, lubricants, such as calcium stearate, stearic acid, magnesium stearate, antioxidants such as butylated hydroxy toluene, antiflatuants such as simethicone and the like.

Optionally, rupturing agents are used to rapidly deliver the pharmaceutical into the recipient's system. A typical rupturing agent is a starch that swells in the presence of water. A preferred rupturing agent is sodium starch glycolate. When ingested, the capsule or pellet swells in the presence of gastric juices and ruptures. In one embodiment of the present invention, the rupturing agent is present inside the microcapsule. As water penetrates the microcapsule, it swells the starch and ruptures the capsule, rapidly delivering the pharmaceutical to the system.

In another embodiment, the rupturing agent is present in the lipid suspension, which ruptures the pellet, but leaves the microcapsules intact. This allows the delayed delivery of the drug farther along in the digestive system, or in the intestines. The present invention is particularly effective in this embodiment, in that the ingested pellet is chewable, yet the pellet cleaves in the lipid suspension when chewed, leaving the microcapsules intact. Tablets or gel capsules, when chewed, typically result in damage to or rupturing of the microcapsules defeating the effectiveness of the microcapsules.

In yet another embodiment, multiple drugs have multiple encapsulations, each containing an rupturing agent. The filming agents used for encapsulation are selected to disintegrate at selected pH conditions, which rupture and release each drug at desired locations in the digestive system.

The process for preparing the above delivery system comprises melting the lipid and mixing with the surfactant. The dry particles are mixed with the melted lipid mixture to form a suspension exhibiting pseudoplastic and/or thixotropic flow properties, and poured or molded to provide solid dosage forms.

The dry particles, which include the pharmaceutical, filler and optional flavorings and additives, are pre-blended and typically have a particle size in the range of from about 50 to 150 microns. The pre-blended particles are gradually added to the heated lipid base until a high solid suspension is obtained, typically in the range of about 60 to 80% particles and from about 40 to 20% lipid.

Slow addition of the dry particles is critical in the production of the device, to insure that the particles are suspended in their micronized state and not as agglomerated clumps. Moreover, rapid addition can cause the mixing process to fail in that the melted suspension will not have the desired flow properties, but instead will be a granular oily mass (a sign of product failure). The mixing step is accomplished in a heated mixing device that insures thorough mixing of all materials with minimal shear, such as a planetary mixer or a scrape surface mixer. After the suspension is formed, the product is poured into molds and allowed to cool. De-molding and packaging are then performed. Alternatively, the suspension can be super-cooled and sheeted in a semi-soft format. The sheet is processed through forming rolls containing a design or configuration that embosses and forms the final shape.

The following examples are to illustrate the claimed invention and are not intended to limit the claims in any way. All of the percentages are by weight unless otherwise indicated.

Examples

Examples I–V were prepared according to the following procedure.

Microencapsulation of the Drug

The pharmaceutical particles were dry-blended with the rupturing agent, (sodium starch glycolate sold under the trademark Explotab® in a Hobart 5 Quart planetary mixer jacketed with a heating mantle. A 4% mixture of the filming agent, (ethylcellulose, sold commercially under the trademark Ethocel®) and ethanol was slowly added to the dry mix thereby forming wet granules. The wet granules were tray dried and screened to a particle of between about 200 and 500 microns.

Forming the Suspension

The first lipid (vegetable stearines sold under the trademark Duratex®) was heated in a Hobart 5 Quart planetary mixer jacketed with a heating mantle in the range of about 140 to 150° F. and melted. The second lipid (98° F. vegetable hard butter sold under the trademark Kalomel®) was added to the jacketed mixer and melted with mixing. The surfactant, lecithin, was added to the lipids with mixing, and the mixture was allowed to cool to about 135° F.

The dry particles, including the microencapsulated pharmaceutical, the flavorings, and the filler (whey) were screened to a particle size in the range of about 200 and 500 microns and dry-blended. The dry particles were slowly added incrementally to the lipid/surfactant mixture with mixing over a period of about 1 hour, to provide a smooth suspension with no lumps or agglomerations. The suspension was molded and cooled to about 70° F. The suspension shrank as it cooled, and easily released from the mold when inverted.

Example I

TABLE A

Microencapsulation of Carprofen
BATCH FORMULA

| Ingredient | Weight (grams) | % |
|---|---|---|
| Carprofen (Pharmaceutical) | 7.580 | 18.95% |
| Ethycellulose (30 gm of 4% ethanol solution) | 1.200 | 3.00% |
| Sodium starch gluconate | 31.220 | 78.05% |
| Totals | 40 | 100.00% |

TABLE B

Forming a Suspension of
Carprofen in a 100 mg Dose
BATCH FORMULA

| Ingredient | Weight (grams) | % |
|---|---|---|
| Vegetable stearine | 0.4536 | 25.20% |
| Vegetable hard butter | 0.1944 | 10.80% |
| Lecithin | 0.0108 | 0.60% |
| Chedlong #1 (flavoring) | 0.2430 | 13.50% |
| Cheese flavor 2517 | 0.0090 | 0.50% |
| Cheese flavor 1200s | 0.0270 | 1.50% |
| Salt | 0.0180 | 1.00% |
| Whey | 0.2642 | 14.68% |
| Microencapsulated carprofen (drug from table A) | 0.5800 | 32.22% |
| Totals | 1.8 | 100.00% |

Example II

TABLE A

Microencapsulation of Enalapril Maleate
BATCH FORMULA

| Ingredient | Weight (grams) | % |
|---|---|---|
| Enalapril maleate (Pharmaceutical) | 1.460 | 3.65% |
| Ethylcellulose (20 gm of 4% ethanol solution) | 0.800 | 2.00% |
| Sodium starch glycolate | 37.740 | 94.35% |
| Totals | 40 | 100.00% |

TABLE B

Forming a Suspension of
Enapril in a 5 mg Dose
BATCH FORMULA

| Ingredient | Weight (grams) | % |
|---|---|---|
| Vegetable stearines | 0.3780 | 25.20% |
| Vegetable hard butter | 0.1620 | 10.80% |
| Sodium starch glycolate | 0.2535 | 16.90% |
| Lecithin | 0.0090 | 0.60% |
| Chedlong #1 (flavoring) | 0.2025 | 13.50% |
| Cheese flavor 2517 | 0.0075 | 0.50% |
| Cheese flavor 1200s | 0.0225 | 1.50% |

TABLE B-continued

Forming a Suspension of
Enapril in a 5 mg Dose
BATCH FORMULA

| Ingredient | Weight (grams) | % |
|---|---|---|
| Salt | 0.0150 | 1.00% |
| Whey | 0.3000 | 20.00% |
| Microencapsulated enapril | 0.1500 | 10.00% |
| (From Table A) | | |
| Totals | 1.5 | 100.00% |

Example III

TABLE A

Microencapsulation of Furosemide
BATCH FORMULA

| Ingredient | Weight (grams) | % |
|---|---|---|
| Furosemide (Pharmaceutical) | 3.66 | 9.15% |
| Ethylcellulose (20 gm of 4% ethanol solution) | 0.80 | 2.00% |
| Sodium starch glycolate | 35.54 | 88.85% |
| Totals | 40 | 100.00% |

TABLE B

Forming a Suspension of
Furosemide in a 12.5 mg Dose
BATCH FORMULA

| Ingredient | Weight (grams) | % |
|---|---|---|
| Vegetable stearines | 0.3780 | 25.20% |
| Vegetable hard butter | 0.1620 | 10.80% |
| Sodium starch glycolate | 0.2535 | 16.90% |
| Lecithin | 0.0090 | 0.60% |
| Chedlong #1 (flavoring) | 0.2025 | 13.50% |
| Cheese flavor 2517 | 0.0075 | 0.50% |
| Cheese flavor 1200s | 0.0225 | 1.50% |
| Salt | 0.0150 | 1.00% |
| Whey | 0.3000 | 20.00% |
| Microencapsulated furosemide | 0.1500 | 10.00% |
| (From Table A) | | |
| Totals | 1.5 | 100.00% |

Example IV

TABLE A

Microencapsulation of Levothyroxine Sodium
BATCH FORMULA

| Ingredient | Weight (grams) | % |
|---|---|---|
| Levothyroxine Sodium (Pharmaceutical) | 0.120 | 0.30% |
| Ethylcellulose (20 gm of 4% ethanol solution) | 0.800 | 2.00% |
| Sodium starch glycolate | 39.080 | 97.70% |
| Totals | 40 | 100.00% |

TABLE B

Forming a Suspension of
Levothyroxine in a 0.4 mg Dose
BATCH FORMULA

| Ingredient | Weight (grams) | % |
|---|---|---|
| Vegetable stearines | 0.3780 | 25.20% |
| Vegetable hard butter | 0.1620 | 10.80% |
| Sodium starch glycolate | 0.2535 | 16.90% |
| Lecithin | 0.0090 | 0.60% |
| Chedlong #1 (flavoring) | 0.2025 | 13.50% |
| Cheese flavor 2517 | 0.0075 | 0.50% |
| Cheese flavor 1200s | 0.0225 | 1.50% |
| Salt | 0.0150 | 1.00% |
| Whey | 0.3000 | 20.00% |
| Microencapsulated Levothyroxine | 0.1500 | 10.00% |
| (From Table A) | | |
| Totals | 1.5 | 100.00% |

Example V

TABLE A

Microencapsulation of Prednisolone
BATCH FORMULA

| Ingredient | Weight (grams) | % |
|---|---|---|
| Prednisolone (Pharmaceutical) | 1.460 | 3.65% |
| Ethylcellulose (20 gm of 4% ethanol solution) | 0.800 | 2.00% |
| Sodium starch glycolate | 37.740 | 94.35% |
| Totals | 40 | 100.00% |

TABLE B

Forming a Suspension of
Prednisolone in a 5 mg Dose
BATCH FORMULA

| Ingredient | Weight (grams) | % |
|---|---|---|
| Vegetable stearines | 0.3780 | 25.20% |
| Vegetable hard butter | 0.1620 | 10.80% |
| Sodium starch glycolate | 0.2535 | 16.90% |
| Lecithin | 0.0090 | 0.60% |
| Chedlong #1 (flavoring) | 0.2025 | 13.50% |
| Cheese flavor 2517 | 0.0075 | 0.50% |
| Cheese flavor 1200s | 0.0225 | 1.50% |
| Salt | 0.0150 | 1.00% |
| Whey | 0.3000 | 20.00% |
| Microencapsulated prednisolone | 0.1500 | 10.00% |
| (From Table A) | | |
| Totals | 1.5 | 100.00% |

What is claimed is:

1. An oral pharmaceutical delivery system comprising:
A. at least one lipid;
B. at least one surfactant; and
C. dry particles having a particle size of greater than about 50 microns,
wherein, the dry particles contain at least one pharmaceutical;
wherein, the dry particles are continuously coated with the lipid and form a homogenous suspension with the lipid;
wherein the suspension exhibits pseudoplastic and/or thixotropic properties, and wherein the suspension is formed or shaped into the appropriate solid dosage form by molding or pouring the suspension when in a liquid or semi-liquid state.

2. The method of claim 1 in which said pharmaceutical particles are microencapsulated with a filming agent, said filming agent comprising ethylcellulose.

3. The method of claim 2 in which said microencapsulated pharmaceutical particles have a particle size of between 200 to 500 microns.

4. The method of claim 2 in which said pharmaceutical particles are microencapsulated with a rupturing agent.

5. The method of claim 4 in which said rupturing agent is sodium starch glycolate.

6. The method of claim 5 in which said lipid source forms 20% to 40% by weight of said suspension, and said dry particles form 60% to 80% by weight of said suspension.

7. The method of claim 6 in which said fillers have a size ranging from 10 to 500 microns in diameter and comprise whey.

8. The method of claim 1 in which said lipid is selected from the group consisting of a hard butter, petroleum wax, vegetable fat or animal stearines.

9. The method of claim 1 in which said lipid suspension contains a rupturing agent.

10. The method of claim 9 in which said rupturing agent is sodium starch glycolate.

11. The method of claim 10 in which the dry particles include artificial flavorings.

12. An oral pharmaceutical delivery system comprising:

A. at least one lipid;

B. at least one surfactant; and

C. dry particles, wherein, the dry particles contain at least one pharmaceutical;

wherein, the dry particles are continuously coated with the lipid and form a homogenous suspension with the lipid;

wherein the suspension exhibits pseudoplastic and/or thixotropic properties, and wherein the suspension is formed or shaped into the appropriate solid dosage form by molding or pouring the suspension when in a liquid or semi-liquid state;

wherein said pharmaceutical particles are present in said suspension as a microencapsulated particle;

wherein said microencapsulated particles have an encapsulating film comprised of ethylcellulose.

13. The pharmaceutical delivery system of claim 12 in which said microencapsulated pharmaceutical particles contain therein a rupturing agent.

14. The pharmaceutical delivery system of claim 13 in which said rupturing agent comprises sodium starch glycolate.

15. An oral pharmaceutical delivery system comprising:

A. at least one lipid;

B. at least one surfactant; and

C. dry particles wherein, the dry particles contain at least one pharmaceutical and at least one filler;

wherein, the dry particles are continuously coated with the lipid and form a homogenous suspension with the lipid;

wherein the suspension exhibits pseudoplastic and/or thixotropic properties;

wherein the suspension is formed or shaped into the appropriate solid dosage form by molding or pouring the suspension when in a liquid or semi-liquid state;

wherein said pharmaceutical particles are present in said suspension as a microencapsulated particle; and wherein said microencapsulated particles have an encapsulating film comprising ethylcellulose.

16. The pharmaceutical delivery system of claim 15 in which said microencapsulated pharmaceutical particles contain therein a rupturing agent.

17. The pharmaceutical delivery system of claim 16 in which said rupturing agent comprises sodium starch glycolate.

18. An oral pharmaceutical delivery system comprising:

A. at least one lipid;

B. at least one surfactant; and

C. dry particles wherein, the dry particles contain at least one pharmaceutical and at least one filler;

wherein, the dry particles are continuously coated with the lipid and form a homogenous suspension with the lipid;

wherein the suspension exhibits pseudoplastic and/or thixotropic properties;

wherein the suspension is formed or shaped into the appropriate solid dosage form by molding or pouring the suspension when in a liquid or semi-liquid state; and wherein said filler comprises whey.

19. The pharmaceutical delivery system of claim 18 in which said lipid system contains a rupturing agent comprising sodium starch glycolate.

20. A method for preparing an oral pharmaceutical delivery system comprising:

melting at least one lipid;

mixing in at least one surfactant to said melted lipid;

mixing in dry particles to said melted lipid and surfactant, wherein said dry particles contain at least one pharmaceutical, and at least one filler;

wherein the dry particles are continuously coated with the lipid and for a homogenous suspension with the lipid;

wherein the suspension exhibits pseudoplastic and/or thixotropic properties, wherein the suspension is formed or shaped into the appropriate dose by molding or pouring the suspension when in a liquid or semi-liquid state; and wherein the lipid suspension contains a rupturing agent comprising sodium starch glycolate.

21. An oral pharmaceutical delivery system comprising:

A. at least one lipid;

B. at least one surfactant; and

C. dry particles, wherein, the dry particles contain at least one pharmaceutical;

wherein, the dry particles are continuously coated with the lipid and form a homogenous suspension with the lipid;

wherein the suspension exhibits pseudoplastic and/or thixotropic properties;

wherein the suspension is formed or shaped into the appropriate solid dosage form by molding or pouring the suspension when in a liquid or semi-liquid state; and wherein said pharmaceutical is selected from the group consisting of analgesics, antibiotics, anti-inflammatory agents, cardiovascular drugs, gastrointestinal medicines, hormones, and laxatives.

22. A method for preparing an oral pharmaceutical delivery system comprising:

melting at least one lipid;

mixing in at least one surfactant to said melted lipid;

mixing in dry particles to said melted lipid and surfactant, wherein said dry particles contain at least one pharmaceutical, and at least one filler;

wherein the dry particles are continuously coated with the lipid and for a homogenous suspension with the lipid;

wherein the suspension exhibits pseudoplastic and/or thixotropic properties, wherein the suspension is formed or shaped into the appropriate dose by molding or pouring the suspension when in a liquid or semi-liquid state; and wherein said pharmaceutical is selected from the group consisting of analgesics, antibiotics, anti-inflammatory agents, cardiovascular drugs, gastrointestinal medicines, hormones, and laxatives.

* * * * *

UNITED STATES PATENT AND TRADEMARK OFFICE
CERTIFICATE OF CORRECTION

PATENT NO. : 6,541,025 B1
DATED : April 1, 2003
INVENTOR(S) : Alvin Kershman and Jeff L. Shear It is certified that error appears in the above-identified patent and that said Letters Patent is hereby corrected as shown below:

<u>Column 8, line 55 through Column 9, lines 1-3,</u>
Delete
"1.  An oral pharmaceutical delivery system comprising:
   A. at least one lipid;
   B. at least one surfactant; and
   C. dry particles having a particle size of greater than about 50 microns,
wherein, the dry particles contain at least one pharmaceutical;
wherein, the dry particles are continuously coated with the lipid and form a homogenous
   suspension with the lipid;
wherein the suspension exhibits pseudoplastic and/or thixotropic properties, and
wherein the suspension is formed or shaped into the appropriate solid dosage form by
   molding or pouring the suspension when in a liquid or semi-liquid state."
and insert in place thereof -- 1.  A method for preparing an oral pharmaceutical delivery system comprising the steps of:
   microencapsulating pharmaceutical particles;
   melting at least one lipid;
   mixing in a surfactant to said melted lipid;
   dry-mixin dry particles comprising at least one filler and said microencapsulated pharmaceutical;
   mixing the dry particles with said melted lipid to form a suspension such that said dry particles are continuously coated by said lipid such that said suspension exhibits pseudoplastic and/or thixotropic properties, and pouring or molding said suspension into a dosage form. --

Signed and Sealed this

Fifth Day of August, 2003

JAMES E. ROGAN
*Director of the United States Patent and Trademark Office*